(12) United States Patent
Weithmann et al.

(10) Patent No.: US 10,270,415 B2
(45) Date of Patent: Apr. 23, 2019

(54) RECEIVING COUPLER FOR CONTACTLESS DATA LINK

(71) Applicant: SCHLEIFRING GMBH, Furstenfeldbruck (DE)

(72) Inventors: Herbert Weithmann, München (DE); Holger Steffens, München (DE); Michael Tekloth, Puchheim (DE)

(73) Assignee: SCHLEIFRING GMBH, Fürstenfeldbruck (DE)

( * ) Notice: Subject to any disclaimer, the term of this patent is extended or adjusted under 35 U.S.C. 154(b) by 86 days.

(21) Appl. No.: 14/996,464

(22) Filed: Jan. 15, 2016

(65) Prior Publication Data

US 2016/0211822 A1    Jul. 21, 2016

(30) Foreign Application Priority Data

Jan. 15, 2015    (EP) .................................... 15151280

(51) Int. Cl.

| A61B 6/00 | (2006.01) |
|---|---|
| A61B 6/03 | (2006.01) |
| H03H 3/00 | (2006.01) |
| H03H 7/00 | (2006.01) |
| H04B 5/00 | (2006.01) |
| H05K 1/02 | (2006.01) |

(52) U.S. Cl.
CPC ............. *H03H 7/004* (2013.01); *A61B 6/032* (2013.01); *A61B 6/56* (2013.01); *H03H 3/00* (2013.01); *H04B 5/0012* (2013.01); *H05K 1/0239* (2013.01)

(58) Field of Classification Search
CPC ......... H04B 5/0012; A61B 6/56; A61B 6/563; A61B 6/032; H03H 3/00; H03H 7/004; H05K 1/0239
See application file for complete search history.

(56) References Cited

U.S. PATENT DOCUMENTS

| 4,730,224 A | 3/1988 | Komatsu | |
|---|---|---|---|
| 5,451,543 A * | 9/1995 | Woo | H01L 21/76816 257/E21.577 |
| 5,530,422 A * | 6/1996 | Harrison | A61B 6/56 340/500 |
| 5,577,026 A * | 11/1996 | Gordon | H01Q 1/38 343/841 |

(Continued)

FOREIGN PATENT DOCUMENTS

EP    2775630 A1    9/2014

OTHER PUBLICATIONS

European Search Report in EP15151280, 7 pages, dated Jun. 18, 2015.

*Primary Examiner* — Chih-Cheng Kao
(74) *Attorney, Agent, or Firm* — Yakov S. Sidorin; Quarles & Brady LLP (57) ABSTRACT

A receiving coupler for large diameter capacitive data links comprises at least two layers of isolating material, having different lengths and being attached to each other. The shorter layer comprises on its outer surface a first pair of conductors, whereas the longer layer comprises a second pair and a third pair of conductors. The conductors are connected to each other by vias. The stack of layers of different lengths can be adapted to various curve radii of transmitting components of a capacitive rotary joint.

16 Claims, 4 Drawing Sheets

(56) References Cited

U.S. PATENT DOCUMENTS

| | | | | |
|---|---|---|---|---|
| 2003/0003776 A1* | 1/2003 | Lohr | .................... | H04B 5/0012 439/1 |
| 2006/0089009 A1* | 4/2006 | Krumme | ................. | H01F 38/18 307/11 |
| 2007/0217174 A1* | 9/2007 | Shen | ................... | H01L 23/3114 361/760 |
| 2007/0262836 A1 | 11/2007 | Voss | | |

\* cited by examiner

RECEIVING COUPLER FOR CONTACTLESS DATA LINK

CROSS-REFERENCE TO RELATED APPLICATIONS

This application claims priority from and benefit of the pending European Application No. 15151280.3 filed on Jan. 15, 2015. The above-mentioned European Application is incorporated herein by reference.

BACKGROUND

1. Field of the Invention

The invention relates to capacitive couplers for non-contacting or contactless signal and data transmission, in particular to capacitive rotating transmission devices like rotary joints. Such transmission devices may be used in computer tomography scanners, also called CT scanners.

2. Description of Relevant Art

Capacitive rotating couplers, also called capacitive rotary joints are used to couple signals and data between parts rotating against each other. For example, in CT scanners, a rotating x-ray tube and an x-ray detector generate high-speed imaging data. The data may be transmitted from the rotating part to the stationary part. Furthermore, control signals for controlling the device and specifically the power supply of the x-ray tube may be transmitted from the stationary to the rotating part and vice versa. Many further applications exist where there is the need to transmit control signals or data between a rotor and a stator like in windmills, revolving transfer machines, bottling plants, packaging machines or placement heads of insertion machines.

A capacitive rotary joint for CT scanners is disclosed in U.S. Pat. No. 5,600,697. A large diameter rotating ring carries a differentially driven strip line guiding a signal along this circumference of the ring. At the stationary side, there is a capacitive coupler picking up the signal from the near field of the strip line. The receiving coupler comprises two lines held orthogonally to the transmission line. To obtain a sufficient coupling efficiency and therefore a sufficient signal level at the receiver, the coupler must be mounted in close proximity to the strip line.

A bidirectional capacitive coupler is disclosed in US 2013/0214614. Here, the channels for the communication from the rotating to the stationary side and vice versa are interleaved.

A noise immune capacitive coupler is disclosed in U.S. Pat. No. 6,956,450 B1. Here, the transmission line is not a strip line, but it is a low pass filter structure, having a pair of transmission line conductors, suitable to suppress high frequency noise. It is terminated at its ends with the characteristic impedance of the line. Due to the pattern, the structure is wider than a strip line with a comparable characteristic impedance. This results in a larger coupling capacitance with a similar coupler layout compared to a strip line.

SUMMARY

The embodiments are directed to provide a receiving coupler that offers an improved coupling capacitance and therefore an improved coupling efficiency and an increased signal level in a capacitive rotary joint, further allowing to increase the distance between the receiving coupler and the transmission line. Furthermore, the receiving coupler should have a simple mechanical and electrical design and may be easily manufactured at low costs.

In an embodiment, a receiving coupler comprises a differential pair of electrical conductors. In contrast to the transmission line at the ring, this conductor pair is not a strip line. A strip line as in the ring for transmission of signals has a characteristic impedance all over its length and is terminated at its ends. At the receiving coupler the signals are picked up by a high impedance receiver. The conductor pair must not have a constant impedance over its length. Furthermore, it is not terminated at its ends. Preferably, the ends are open and a receiving amplifier is preferably connected at the center of the conductor pair. To obtain a sufficient coupling capacitance to the strip line of the transmitting side, the conductor pair must either have a significant length or a close distance to the transmission line. The length of the conductor pair is limited by the bandwidth, as it must be short compared to the wavelength of the transmitted signal. To obtain a close proximity over the whole length of the transmission line, the conductor pair must be curved with a similar radius as the transmission line which is in most cases bent to a ring. Therefore, the conductor pair is often mounted to a flexible printed circuit. Such a flexible printed circuit needs a holding structure holding the flexible printed circuit in an appropriate shape. The flexible printed circuit must be held to the holding structure, for example by an adhesive tape. The adhesive tape and the holding structure both affect the electrical field around the conductor pair and have an adverse effect to signal reception. Things get worse, if the receiving coupler is not perfectly aligned with the transmission line. If the alignment is not parallel, but under an angle, the receiving coupler may affect signal transmission in the strip line and cause the strip line to radiate RF signals. Therefore, the use of a flexible printed circuit board is critical and complex.

According to one embodiment, the receiving coupler has an outer surface which approaches a radius by at least two levels or layers of a supporting structure. Preferably, the supporting structure is a printed circuit board, preferably a non-flexible printed circuit board. It is further preferred, if the conductor pairs at the different levels are connected via through-holes.

By an appropriate selection of the number of levels and the height of the levels, a good approximation to any required radius can be obtained. For a large radius, there may be comparatively flat levels, whereby a low number of levels may be sufficient. For a comparatively small radius, it may be preferred to have comparatively higher levels. It may further be beneficial to have a larger number of levels. In a preferred embodiment, there are two levels, whereby the height of the levels is adjusted to the radius. Such different levels may be formed by stacking multiple layers of a material or removing parts of the upper layers.

In one embodiment, a receiving coupler comprises at least two layers of an insulating material. Such a material may be a printed circuit board material which for example may be fiber-reinforced epoxy material. It may also be any other suitable material providing electrical isolation and preferably providing low dielectric losses. It is further preferred, if the material has a low dielectric constant to reduce parasitic capacitance to the background. There is at least one upper layer and at least one lower layer of the isolating material. The upper layer has a pair of upper conductors. This pair of upper conductors is at the top of the upper layer and it preferably is adapted to the strip line of a transmission line from which signals are to be received. Preferably, the upper conductors have a similar width and a similar distance as the strip lines of the transmission line. This ensures a maximum coupling efficiency due to the maximum coupling capacitance between the receiving coupler and the transmission line. The lower layer is arranged below the upper layer. The lower layer has a larger length than the upper layer. It preferably has the same or a similar width. Preferably, the lower layer and the upper layer are centered with each other. Preferably, the lower layer extends in length on both sides over the upper layer. Most preferably, the lower layer has at least one pair of lower conductors at at least one side extending beyond the upper layer. For the case the lower layer is centered to the upper layer, the sides extending over the upper layer have the same size, and therefore it is preferred that the lower conductors have the same size on both sides. It is further preferred, if the upper layer is electrically connected to the lower layer. This connection preferably is located at an outer side of the upper layer. This may result in a small overlapping region of the upper layer and the lower layer. Either the upper layer or the lower layer or both layers may be covered by additional dielectric material which may be a thin coating which may act as a protection for corrosion or which may also be a thick layer like a printed circuit board or any other material resulting in increased mechanical stability and/or protection. There may be any number of intermediate layers, either of insulating and/or conducting materials between the lower layer and the upper layer. Preferably, the layers have varying lengths, with the lowest layers having the largest length, the length further being reduced to the top layer having the smallest length. By adjusting the number, the height and the length of the layers, nearly any form of a receiving coupler may be made.

Preferably, the upper and lower conductors are aligned to a common axis. Most preferably, they are aligned parallel to transmission line conductors of a transmission line.

The receiving coupler may be attached to a receiver board, further being part of the receiving component. Preferably, the receiver board comprises at least a receiver amplifier. It may further comprise additional electronic components, like passive components, e. g. for filtering the received signals, or active components for signal amplification and/or processing. It may further comprise an electro-optical converter to provide light output which may be connected to an optical fiber. Preferably, the receiving coupler is soldered to the receiver board.

The receiving coupler may be glued and/or laminated and/or soldered and/or screwed and/or bolted and/or connected to the receiver board or may be part of the receiver board.

According to another embodiment, a transmitting/receiving assembly is provided. This assembly comprises a receiving component and a transmitting component which are connected electrically and mechanically by at least one connecting element. Preferably, the connecting element is a part of the receiving component. Preferably, the receiving coupler is a part of the receiving component. It may be a simple coupler as known from prior art, for example comprising a fixed or flexible printed circuit board. Preferably, there is an embodiment as described above, which comprises a plurality of layers of isolating material. Preferably, at least one of these layers is extended outwards of the receiving coupler forming a connecting element. It is further preferred, if the transmitting component is fixedly attached to the connecting element and most preferably electrically connected thereto. The electrical connection may be made by vias or through holes. It is further preferred, if an electronic module is attached to the transmitting/receiving assembly. There may be a connector for connecting and/or disconnecting the electronic module. In another embodiment, there may be a fixed connection like a soldering connection between the electronic module and the other components of the transmitting/receiving assembly. Most preferably, the electronic module is connected close to the receiving component to keep the length of the sensitive receiving lines as short as possible. It is further preferred, if there is at least one shielding layer between the electrical lines of the receiving component and the electrical lines of the transmitting component. By using this assembly, the spatial relationships between the receiving component and a transmitting component are predetermined. Therefore, the receive antenna can be aligned to the transmit antenna by adjusting the transmit/receive assemblies of rotor and stator radially and axially by using spacers and rulers.

Although some of the embodiments described herein relate to a data link for CT scanners and a CT scanner having such a data link, the embodiments may be used in any other application, where a high-speed data link is required. Such applications may be any other scanner, which for example may use a microwave scanning system, or any scanner for example for scanning of luggage or other materials, like wood, plastic or composite structures.

A further embodiment relates to a method for transferring data between a rotating and a stationary part, as described herein.

Further embodiments relate to rotary joints for CT scanners and CT scanners comprising rotary joints as described herein.

Another embodiment relates to a method for manufacturing a receiving coupler. Preferably, parts of a layer of material of an upper surface of an assembly comprising layers of isolating material and conductors are selectively removed or added. Removing may comprise at least one step of machining or cutting.

In a further embodiment multiple layers may be added by gluing, laminating or molding or any other method.

Capacitive rotating couplers which serve for data transmission typically for data rates of 1 to 10 Gbit/s typically are combined to a rotary joint with contacting sliprings for data and power transmission. Another preferred configuration is with inductive contactless power transmission where especially bidirectionally configured capacitive links are used.

A bidirectional arrangement of the links is especially useful for transmission in a bidirectional link as e.g. Gigabit Ethernet.

BRIEF DESCRIPTION OF THE DRAWINGS

In the following, the invention will be described by way of example, without limitation of the general inventive concept, on examples of embodiment and with reference to the drawings.

Embodiments of the invention may be subject to various modifications and alternative forms. Specific embodiments of the invention are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

In the following embodiments, reference is made to an upper layer, lower layer, upper conductors and lower conductors. These relate to an orientation as shown in the Figures, specifically in FIG. 2. It is obvious that such a receiving coupler may be oriented in any orientation in three-dimensional space. The terms "upper" and "lower" are only used for simplification of explanation.

Figure 1:
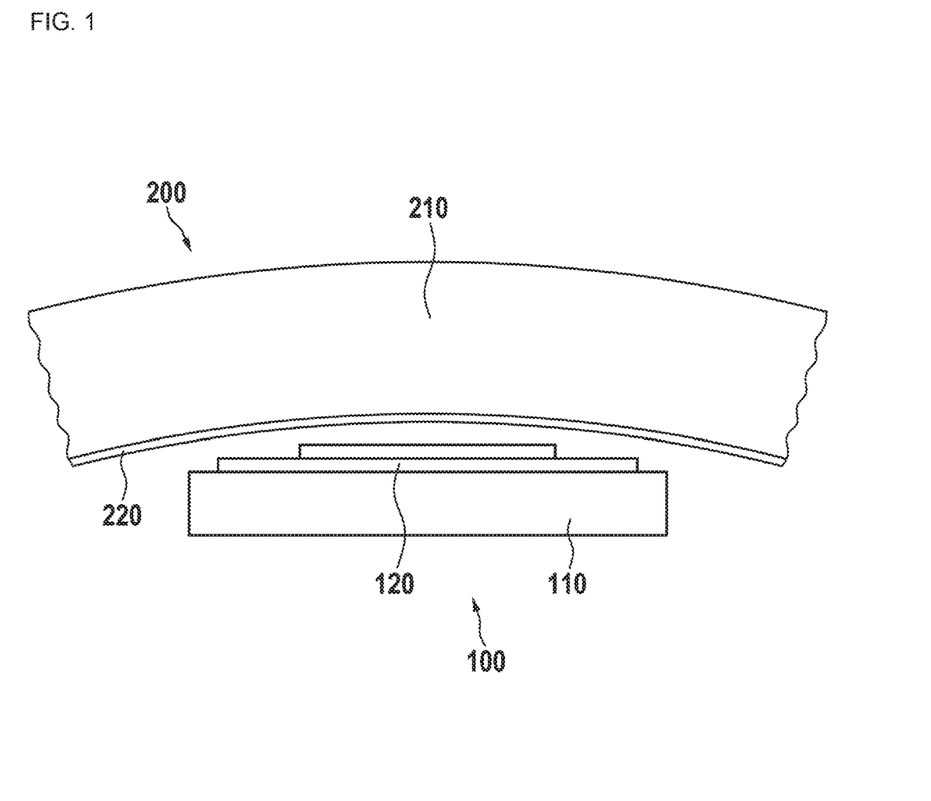
FIG. 1 shows a first embodiment.

In FIG. 1, a first embodiment is shown. A contactless rotary joint which for example may be used in a computed tomography (CT) scanner may comprise a transmitting component 200 and a receiving component 100. The transmitting component 200 preferably is connected to the rotating part of a CT scanner gantry, whereas the receiving component 100 is connected to the stationary part for coupling data from the rotating to the stationary part of the CT scanner. The transmitting component 200 preferably comprises a transmitter support 210. This transmitter support may be a circular plastic carrier. It may also comprise metal or other materials suitable for supporting a structure of the required size. A typical CT scanner rotary joint has a diameter in a range between 1 and 1.5 meters. In this embodiment, the transmitter support 210 bears a transmission line 220 at its inner side. It may also have the transmission line at the outer side. There may also be multichannel embodiments having at least one transmission line at the inner side and at least one transmission line at the outer side. The receiving coupler 120 is arranged at the other component, which preferably is the stationary component of a CT scanner, in a comparatively small distance to the transmission line for coupling signals. The distance must be larger than the maximum run out of the rotating part plus additional tolerances from manufacturing, aging, and others. In a typical CT scanner environment, this distance may be between 2 and 10 millimeters. The receiving coupler 120 may be mounted to a receiver board 110 which may hold electronic components for amplification, forming filtering or processing of a signal received by the receiving coupler 120.

Figure 2:
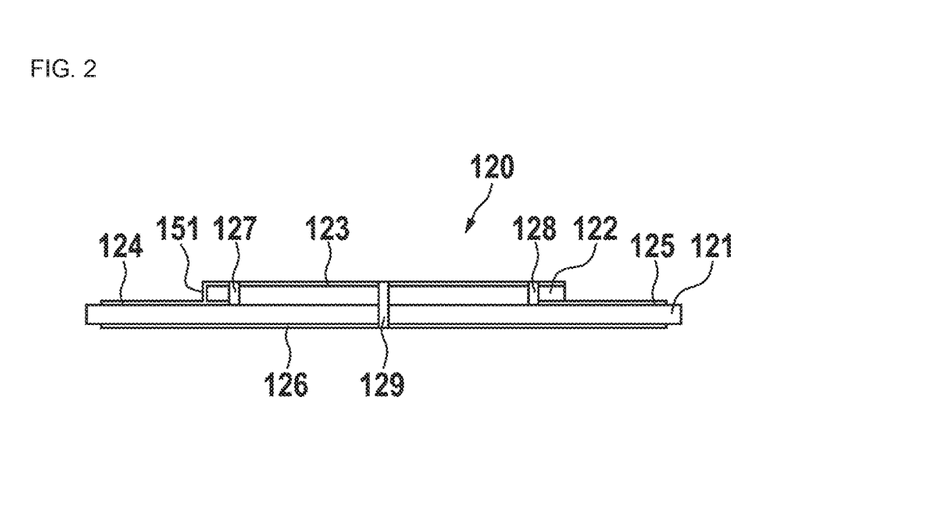
FIG. 2 shows a sectional side view of a receiving coupler.

In FIG. 2, a sectional side view of a receiving coupler 120 is shown. The receiving coupler 120 basically coupler comprises a lower layer 121 and an upper layer 122, both made of electrically isolating material. There is a pair of other conductors 123 on top of the upper layer 122. Furthermore, there are two pairs of lower conductors 124, 125 on top of the lower layer 121. A first pair of lower conductors 124 is at a first side of the lower layer 121, whereas a second pair of lower conductors 125 is at a second side of lower layer 121. Preferably, the lower layer 121 and the upper layer 122 are centered. It is further preferred, if the first pair of lower conductors 124 has the same length as the second pair of lower conductors 125.

The upper conductors 123 are electrically connected to the lower conductors 124, 125. This connection is preferably done by through-hole or vias 127, 128, which preferably are holes through the upper layer with a metalized inner surface or filled by an electrically conductive material. This means that the vias may also be realized by implementing embedded passive components into the isolating material. Furthermore, there may be a bottom conductor 126 at the bottom of the lower layer 121. It is further preferred, if the bottom conductor 126 is electrically connected to at least one of the upper conductors or lower conductors. Preferably, this connection is made by a center via 129 and/or a metallization of the edge of at least one layer. A larger edge metallization 151 may be used to hold multiple layers together. Most preferably, it is connected to the upper conductors. In an alternative embodiment, the bottom conductor may be a ground conductor or a ground plane. Also signals can be contacted by partial metallization e.g. of a half round indentation of the edge.

Figure 3:
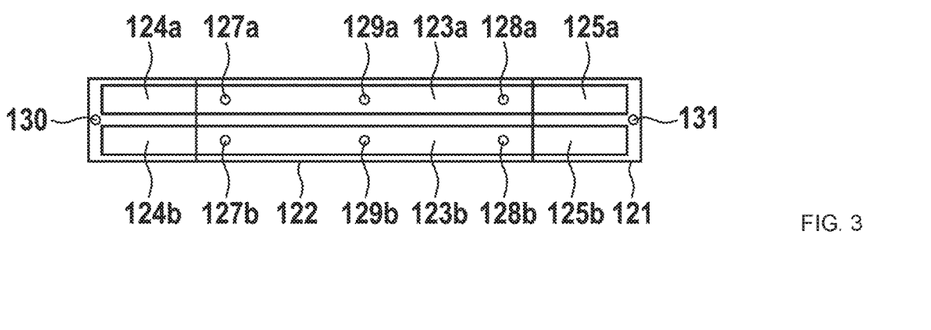
FIG. 3 shows a top view of a receiving coupler.

In FIG. 3, a top view of a receiving coupler is shown. Here, the pair of conductors can be seen. The reference numbers are the same as in the previous Figures, with added letters a, b. The letter "a" refers to a first conductor of the pair of conductors, whereas the letter "b" refers to the second conductor of the pair of conductors. Preferably, both conductors are made symmetrical. For example, the pair of upper conductors 123 comprises a first upper conductor 123a and a second upper conductor 123b. There may further be at least one mounting or centering hole 130, 131.

Figure 4:
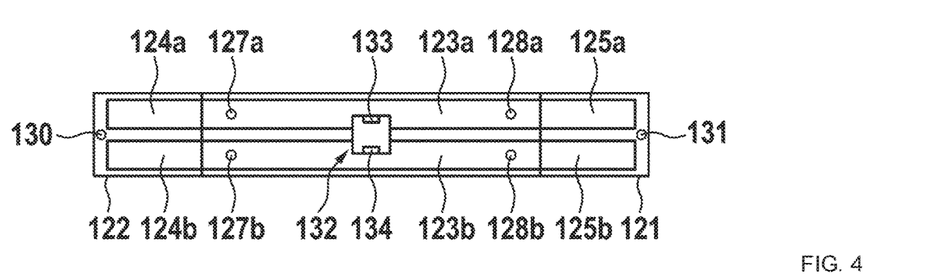
FIG. 4 shows a further embodiment of a receiving coupler.

In FIG. 4, a further embodiment of a receiving coupler is shown. Here, the through-holes of the center vias 129a,b are replaced by a different design. There may be a hole 132 which may be round or rectangular. Preferably, this hole has conductive surfaces 133, 134 at its inner side to connect the upper conductors 123 with the bottom conductors 126.

Figure 5:
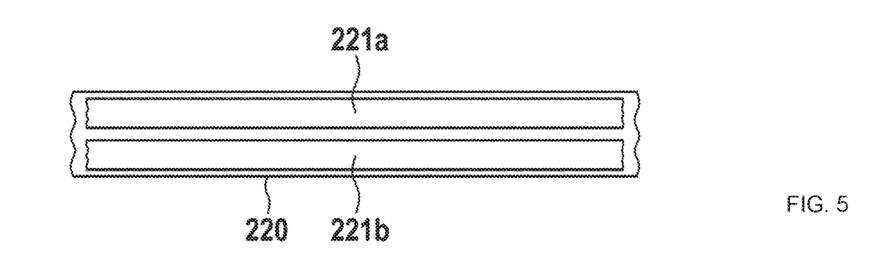
FIG. 5 shows an embodiment of a transmission line.

In FIG. 5, an embodiment of a transmission line 220 is shown. On a dielectric or isolating material, there is a pair of transmission line conductors 221a, 221b. The pair of transmission line conductors is preferably symmetrical and most preferably a pair of strip lines, most preferably configured as differential strip lines. It is further preferred, if the size of the conductors as shown in the previous Figures of the receiving coupler matches the size (width and distance) of the transmission lines. Alternatively, they may have a slightly larger distance and a slightly smaller width.

Figure 6:
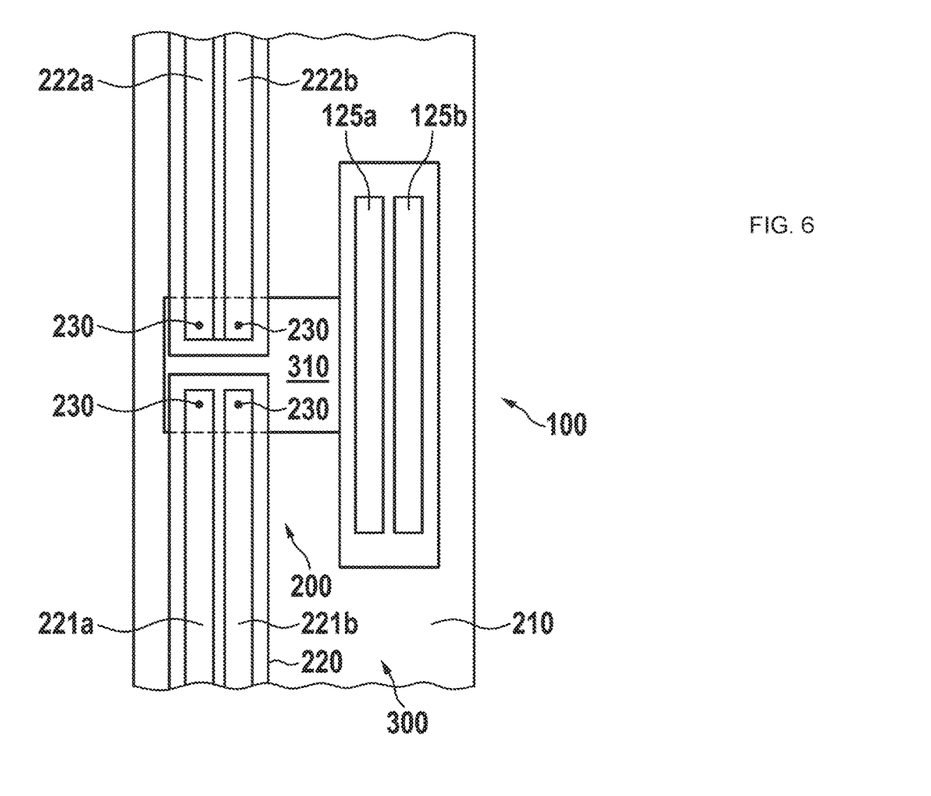
FIG. 6 shows a transmitting/receiving assembly.

FIG. 6 shows a transmitting/receiving (that is, transceiving) assembly 300 comprising a receiving component 100 and a transmitting component 200. Preferably, the receiving component 100 has a structure as described in the other figures, but there may also be a flat or flexible printed circuit board. Furthermore, there is a transmitting component 200 comprising transmission line conductors 221, 222 or any other at a great structure for guiding RF signals, preferably without radiating them. The transmitting component 200 is electrically and mechanically connected via a connecting element 310 to the receiving component 100. It is preferred, if the connecting element 310 is part of the receiving component 100. The connecting element preferably is a printed circuit board or a printed circuit board layer.

Figure 7:
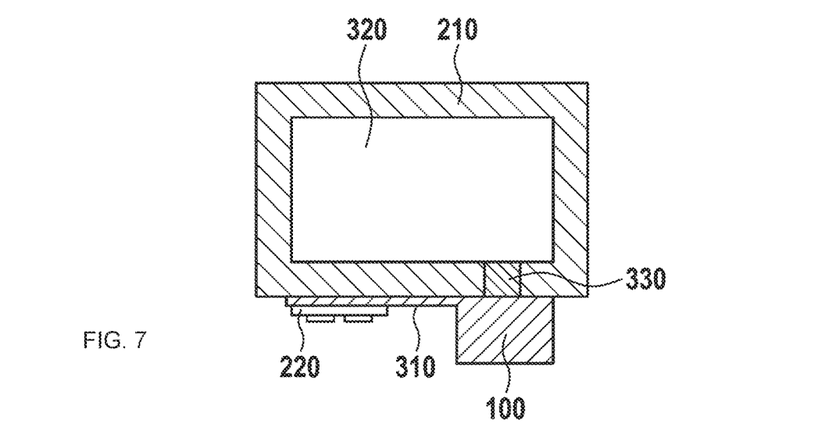
FIG. 7 shows a transmitting/receiving assembly in a sectional view.

FIG. 7 shows a transmitting/receiving assembly in a sectional view. It is further preferred, if an electronic module 320 is attached to the transmitting/receiving assembly 300. The electronic module may be connected by a connector 330 which may be a coaxial connector or a multi pin PCB connector. The transmitting/receiving assembly 300 as shown herein offers a fixed spatial relationship between the receiving component 100 and the transmitting component 200. It further offers a well-defined electrical connection. During assembly it is no more necessary to solder RF connections. Furthermore, it results in a comparatively compact size. It is preferred that the receiving element 100 at the position of the receive coupler 125 has the same thickness as the receive element at the position of the transmitter support 210 and/or connecting element 310 with the transmitting component 200 mounted.

Figure 8:
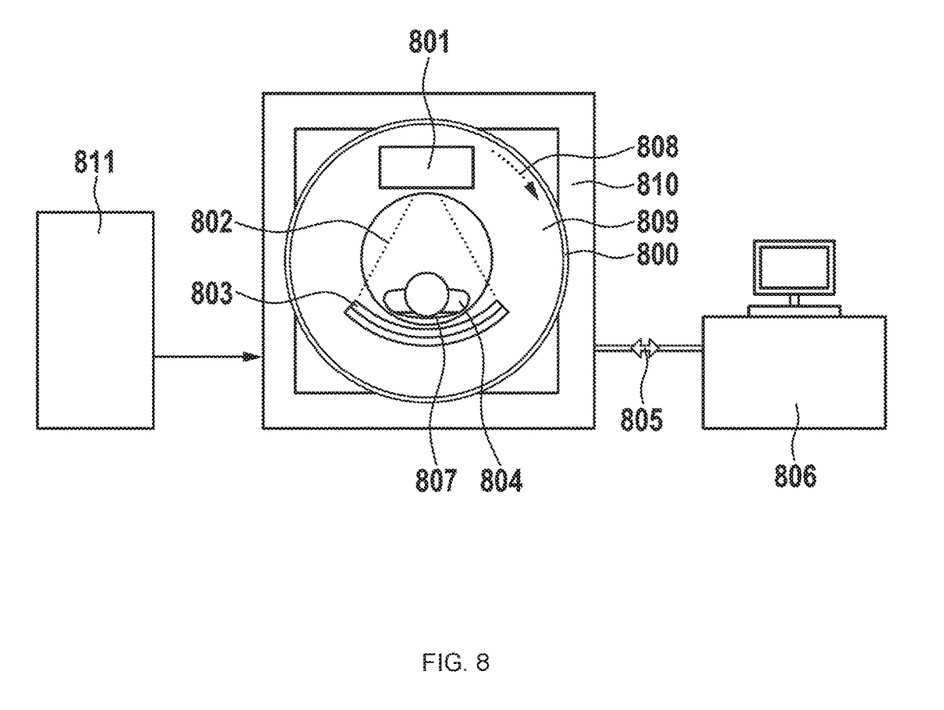
FIG. 8 shows a CT scanner gantry

FIG. 8 shows schematically a CT (Computed Tomography) scanner gantry. The stationary part is suspended within a massive frame 810. The rotating part 809 of the gantry is rotatably mounted with respect to the stationary part and rotates along the rotation direction 808. It supports an X-ray tube 801 for generating an X-ray beam 802 that radiates through a patient 804 lying on a table 807 and which is intercepted by a detector 803 and converted to electrical signals and imaging data thereof. Electrical power from power supply unit 811 may be transmitted by a slipring (not shown) to the rotating part. The data obtained by the detector 803 are transmitted via contactless rotary joint 800 to an evaluation unit 806 by means of a data bus or network 805.

It will be appreciated to those skilled in the art having the benefit of this disclosure that this invention is believed to provide receiving coupler for a contactless data link. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS 100 receiving component
110 receiver board
120 receiving coupler
121 lower layer
122 upper layer
123 upper conductors
124, 125 lower conductors
126 bottom conductor
127, 128 vias
129 center via
130, 131 mounting holes
132 hole
133, 134 conductors
151 edge metallization
200 transmitting component
210 transmitter support
220 transmission line
221 transmission line conductor
222 transmission line conductor
230 vias
300 transmitting/receiving assembly
310 connecting element
320 electronic module
330 connector
800 contactless rotary joint
801 x-ray tube
802 x-ray beam
803 x-ray detector
804 patient
805 network
806 evaluation unit
807 patient table
808 rotation direction
809 rotating part
810 frame
811 power supply unit

The invention claimed is:

1. A receiving coupler for a capacitive rotary joint, the rotary joint having a transmitting component and a receiving component, the receiving coupler representing a part of the receiving component, the receiving coupler comprising:
   at least an upper layer of isolating material having a first length and a lower layer of isolating material having a second length,
   said upper layer having a first upper surface thereof, said lower layer having a second upper surface thereof, the second upper surface facing said upper layer;
   wherein said upper layer bears on the first upper surface at least one pair of upper conductors, and
   wherein said lower layer bears on the second upper surface at least one pair of lower conductors,
   wherein upper conductors from the at least one pair of the upper conductors are electrically connected to lower conductors from the at least one pair of the lower conductors, and
   wherein the second length is longer than the first length,
   wherein conductors of the upper conductors and the lower conductors of the at least said upper layer and said lower layer are dimensioned to be oriented along the circumference of the transmitting component when operably cooperated with the transmitting component.

2. A receiving coupler according to claim 1, wherein said upper layer has a first width and said lower layer has a second width, the first and second widths being equal.

3. A receiving coupler according to claim 1, wherein the lower conductors from the at least one pair of the upper conductors are connected to the upper conductors from the at least one pair of the upper conductors through at least one of i) a via and b) edge metallization.

4. A receiving coupler according to claim 1, wherein the lower layer is centered with respect to the upper layer.

5. A receiving coupler according to claim 1, further comprising a bottom conductor at a bottom surface of the lower layer.

6. A receiving coupler according to claim 5, wherein the bottom conductor is electrically connected to an upper conductor from the at least one pair of upper conductors.

7. A receiving coupler according to claim 5, wherein the bottom conductor is connected to an upper conductor, from the at least one pair of upper conductors, by a through-hole or a via.

8. A receiving component for a capacitive data link comprising the receiving coupler according to claim 1 and a receiver board, the receiver board having at least one of active electronic components and passive electronic components.

9. A transceiving assembly for a capacitive data link comprising:
   a transmitting component comprising a plurality of transmission lines, electrically and mechanically connected by a connecting element and
   a receiving coupler, including
      at least an upper layer of isolating material having a first length and a lower layer of isolating material having a second length,
      said upper layer having a first upper surface thereof, said lower layer having a second upper surface thereof, the second upper surface facing said upper layer;

wherein said upper layer bears on the first upper surface at least one pair of upper conductors, and wherein said lower layer bears on the second upper surface at least one pair of lower conductors, wherein the upper conductors from the at least one pair of the upper conductors are electrically connected to the lower conductors from the at least one pair of the lower conductors, and wherein the second length is longer than the first length, and wherein conductors of the upper conductors and the lower conductors of the at least said upper layer and said lower layer are dimensioned to be oriented along a circumference of the transmitting component when operably cooperated with the transmitting component.

10. A transceiving assembly according to claim 9, further comprising a receiving component, wherein the receiving coupler forms a part of the receiving component, wherein the connecting element is at least one of a printed circuit board and a part of the receiving component.

11. A rotary joint comprising at least one receiving component according to claim 8 and a transmitting component comprising at least one transmission line.

12. A rotary joint comprising at least one transceiving assembly according to claim 9.

13. A CT scanner comprising at least one rotary joint according to claim 11.

14. A CT scanner comprising at least one rotary joint according to claim 12.

15. A method for manufacturing a receiving coupler for a capacitive rotary joint, the capacitive rotary joint including a receiving component and a transmitting component, the method comprising:

forming an assembly including
(i) at least an upper layer of isolating material having a first length and a lower layer of isolating material having a second length, said at least the upper layer and the lower layer dimensioned to be oriented along the circumference of the transmitting component when the receiving coupler is operably cooperated with the transmitting component;
wherein said upper layer has a first upper surface thereof, said lower layer having a second upper surface thereof, the second upper surface facing said upper layer;
(ii) at least one pair of upper conductors on the first upper surface of said upper layer; and
(iii) at least one pair of lower conductors on the second upper surface of said lower layer,
wherein upper conductors from the at least one pair of upper conductors are electrically connected to lower conductors from the at least one pair of the lower conductors, and wherein the second length is longer than the first length,
and
selectively removing parts of a layer of material of an upper surface of the assembly.

16. A method according to claim 15, wherein the selectively removing comprises at least one of machining and cutting.

* * * * *